United States Patent [19]

Lang et al.

[11] Patent Number: 5,327,356

[45] Date of Patent: Jul. 5, 1994

[54] EMISSIONS SPECTRAL RADIOMETER/FUEL FLOW INSTRUMENT

[75] Inventors: Fred D. Lang; Steven K. Petrie, both of Livermore; Arnaldo G. Dall'Era, Mountain View, all of Calif.

[73] Assignee: Wahlco Environmental Systems, Inc., Santa Ana, Calif.

[21] Appl. No.: 908,525

[22] Filed: Jun. 29, 1992

Related U.S. Application Data

[63] Continuation of Ser. No. 450,687, Dec. 14, 1989, abandoned.

[51] Int. Cl.$^5$ ............... G01N 21/17; G01N 21/01
[52] U.S. Cl. ........................ 364/498; 356/216; 250/338.5
[58] Field of Search ............ 364/496, 498, 550, 551.01; 73/112; 356/216; 436/76; 236/15 E; 250/338.5, 339, 372

[56] References Cited

U.S. PATENT DOCUMENTS

| | | | |
|---|---|---|---|
| 4,685,072 | 8/1987 | Johnson et al. | 364/551.01 |
| 4,801,209 | 1/1989 | Wadlow | 364/498 |
| 4,867,563 | 9/1989 | Wurm et al. | 364/498 |
| 4,941,112 | 7/1990 | Nepveu de Villemarceau et al. | 364/496 |
| 5,210,702 | 5/1993 | Bishop et al. | 364/496 |

Primary Examiner—Thomas G. Black
Assistant Examiner—Michael Zanelli
Attorney, Agent, or Firm—Howard E. Sandler; Stephen Donovan

[57] ABSTRACT

An apparatus for measuring the combustion effluent of a fossil-fired system with high accuracy as required for the determination of fuel flow rate and boiler efficiency.

9 Claims, 9 Drawing Sheets

EMISSIONS SPECTRAL RADIOMETER/FUEL FLOW INSTRUMENT

This is a continuation of application Ser. No. 07/450,687 filed on Dec. 14, 1989, now abandoned.

CROSS-REFERENCE TO RELATED APPLICATION

The present invention is related to the copending patent application for a method for Determining Fuel Flow and Thermal Efficiency for Fossil-Fired Steam Generator Systems, U.S. Ser. No. 07/450,686, filed concurrently herewith on Dec. 14, 1989.

BACKGROUND OF THE INVENTION

1. Field of the Invention

The present invention relates to apparatus which is used for measuring the constituents in the combustion exhaust gas effluent of a fossil-fired steam generator or boiler system. More particularly, the invention relates to an apparatus which measures with extreme accuracy the concentrations of $CO_2$ and superheated water as produced from the fossil fuel combustion process so that the fuel flow and thermal efficiency of fossil-fired systems can be determined by thermodynamics for monitoring the operation of such a system.

The importance of accurately determining thermal efficiency is critical to the thermal performance monitoring of any fossil-fired system. If practical day-to-day improvements in efficiency are to be made, and/or corrections to thermally degraded equipment are to be found and corrections taken, then accuracy in determining thermal efficiency is an obvious necessity. The art of tracking the efficiency of a conventional power plant or any fossil-fired system lies fundamentally in measuring the useful output and the total energy flow of the input fuel.

The art of measuring the useful output of a conventional fossil-fired system is highly developed. The useful output can be either the steam flow produced or the subsequent electrical power generated via, commonly, steam expansion in turbines. Measuring the total energy flow of the input fuel, on the other hand, has traditionally caused significant problems, especially for coal-fired power plants. Measurement of the energy flow of the input fuel requires knowledge of the heating value of the fuel and its mass flow rate.

The present invention is specifically designed for the purpose of measuring the combustion effluent with extreme accuracy whereby the mass flow rate of the input fuel can be thereby calculated from thermodynamics without direct measurement of the input fuel flow rate. The embodiment of the invention is called an "Emissions Spectral Radiometer/Fuel Flow" instrument, or ESR/FF instrument.

2. Description of the Prior Art

Present industrial techniques for measuring or analyzing the composition of combustion effluent of a fossil-fired system include: sampling the gas and analyzing with gas chronography (for CO, $CO_2$, and $O_2$ and unburned hydrocarbons); sampling the gas and analyzing using spectrographic absorption of ultraviolet or infrared radiation (for CO, $CO_2$, $H_2O$, $O_2$ and unburned hydrocarbons); sampling the gas and reacting it with certain chemicals which thus determines concentrations (for $CO_2$, $O_2$ and other gases); in-situ detection of $O_2$ by zirconium hydride; and in-situ spectrographic absorption of ultraviolet or infrared radiation (for CO, $CO_2$, $H_2O$, $O_2$ and unburned hydrocarbons). All of these techniques have been in general industrial use for many years. All known techniques involve obtaining samples of the combustion gas and its subsequent analysis in a laboratory environment, except use of in-situ spectrographic absorption techniques and the use of zirconium hydride for $O_2$ detection.

SUMMARY OF THE INVENTION

The present invention is a spectral radiometer for detection of emission gases, called the Emissions Spectral Radiometer/Fuel Flow instrument (ESR/FF instrument), for the end purpose of measuring fuel flow and thermal efficiency for fossil-fired systems. It includes a source instrument and a detector instrument which are comprised of several elements.

The source instrument of the ESR/FF includes a radiation source called a lamp which produces essentially pure, black body radiation in the infrared spectrum. A reflector is provided adjacent to the lamp and partially surrounding it which produces parallel infrared radiation and directs it across the combustion gas emission duct of the fossil-fired unit. A rotating cage assembly is provided which encloses the radiation source and the reflector. The cage has at least one opening therein aligned with the reflector to allow the parallel radiation to escape from the cage assembly as it rotates to provide an alternating flow of radiation (and then no radiation) across the exhaust gas duct.

The ESR/FF also includes a detector instrument which is disposed on the opposite side of the exhaust gas duct across from the source instrument. The detector instrument includes an optical array of reflector optics which causes the parallel radiation received from the source instrument to form a line image of finite length on a first focus point and then to form a second focused image at an infrared detector.

A rotating circular variable filter is disposed at the first focus point of said optical array. An optical slit is disposed in the path of the radiation immediately in front of the circular variable filter, and an infrared radiation detector is disposed at the second focus point of the optical array for receiving the modified radiation for analysis and generating signals which are passed to the analytical computer.

OBJECTS OF THE INVENTION

It is therefore an important object of the present invention to provide an apparatus for accurately measuring the concentrations of $CO_2$ and superheated water which are produced from the combustion process of fossil fuels.

It is another object of the present invention to provide an apparatus for generating essentially pure black body parallel radiation in the infrared spectrum for the purpose of creating a known and highly predictable spectra of radiation by which referenced calculations of the unabsorbed radiation can be made.

It is a further object of the present invention to provide an optical array using reflectors for an infrared radiation detector instrument which folds the radiation for imaging on a circular variable filter and focusing the same on a detector unit.

Other objects and advantages of the present invention will become apparent when the apparatus of the present invention is considered in conjunction with the accompanying drawings.

DESCRIPTION OF THE PREFERRED EMBODIMENT

The Source Instrument

Reference is made to the drawings for a description of the preferred embodiment of the present invention wherein like reference numbers represent like elements on corresponding views.

Figure 1:
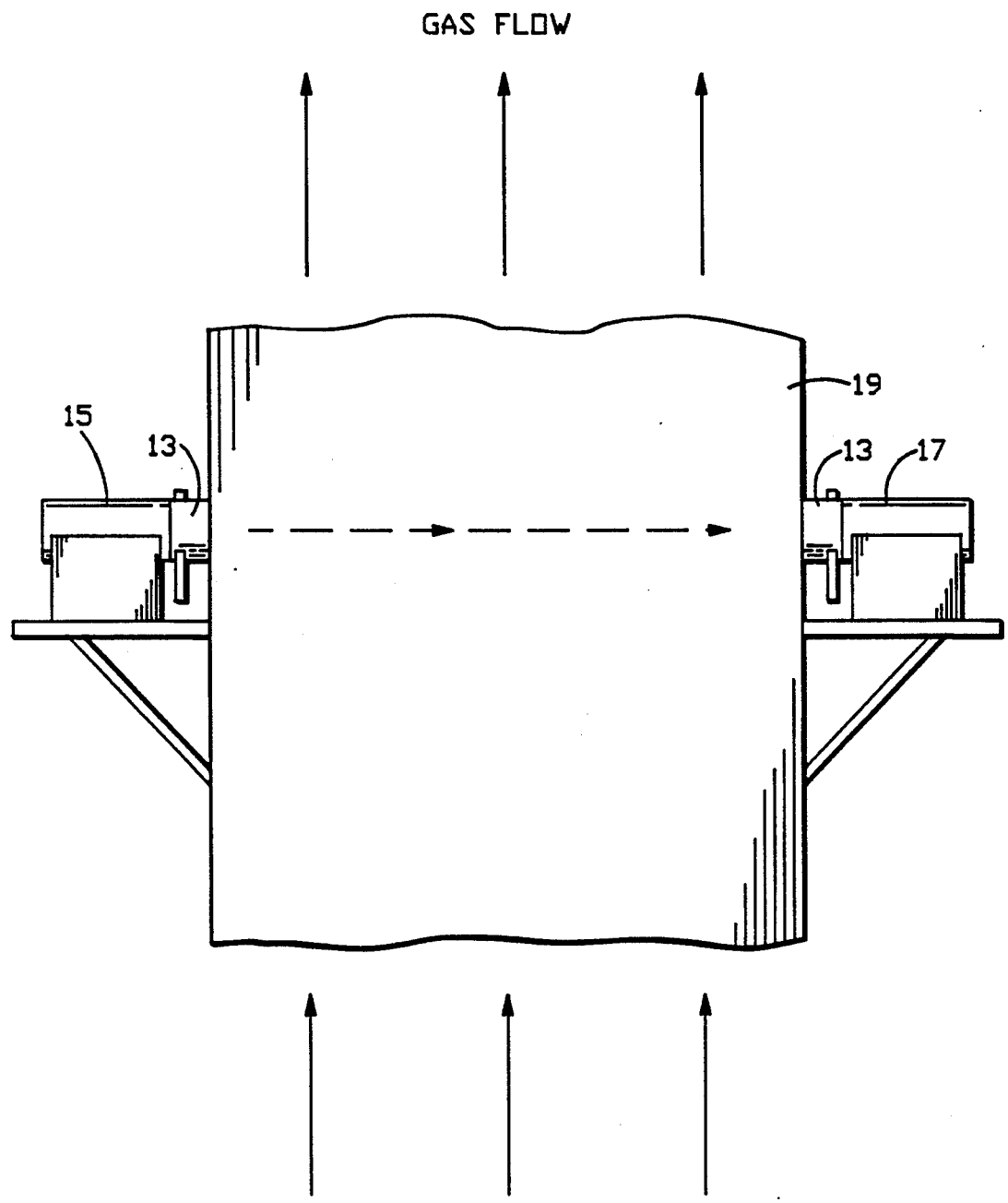
FIG. 1 is a side elevation of the emissions spectral radiometer of present invention illustrating the aligned positioning of the source and detector instruments located on opposite sides of a combustion exhaust gas duct.

The spectral radiometer of the present invention for measuring fuel flow, hereafter designated ESR/FF, includes both a radiation source instrument 15 and a radiation detection instrument 17 which are aligned and disposed at opposite sides of a combustion gas effluent duct 19 as shown in FIG. 1.

A radiation source is provided for producing essentially pure black body radiation in the infrared spectrum. The radiation generator consists principally of a graphite rod 21 which is electrically heated to between 1100 to 1700 degrees Kelvin. It has an emissivity of at least 0.90 which denotes essentially pure black body radiation in the infrared spectrum. More importantly, use of a pure graphic rod (thus a black irradiator) implies that the distribution of radiation energy as a function of wavelength can be predicted by Planck's equation. This rod, called the lamp, is mounted on a pair of supports 23 which are secured to a support bench 25 and are provided with cooling fins 27. The rod is enclosed in an optical sapphire tube which is purged and back-filled with an inert gas. End caps are placed on the tube's end which also connect to the graphite rod for electrical contact. The lamp's manufacturer is ILC Technology of Sunnyvale, Ca.

A reflector 29 is secured to the support bench 25 adjacent to and partially surrounding said rod 21. This reflector causes parallel infrared radiation from the lamp emission to be directed across the combustion exhaust gas duct 19. In its preferred form, this reflector is an elongated parabolic shape which encloses the rod horizontally therein and directs the generated radiation horizontally across the gas duct. The reflector is gold platted and produces reasonably parallel infrared radiation which is directed through a flat optical sapphire window 31 located in the combustion gas duct wall.

The reflector 29 and lamp 21 are enclosed within a rotating cage assembly 33 having at least one opening 35 in the cage assembly aligned with the reflector to allow the parallel radiation to escape from the cage assembly as it rotates to provide an alternating flow of radiation across the exhaust gas duct. In the preferred embodiment, two open windows 35 are provided in the cage on opposite sides thereof. The cage assembly has been selected to rotate at 2,250 RPM. This speed of rotation allows sampling of the incident radiation at a natural response frequency of 750 Hz or 20 samples per cage revolution. This sampling frequency provides three samples each time the cage is fully opened and fully closed allowing averaging of the sample reading over three points which is more desirable than two which would not allow a midpoint determination.

A stationary reflector shroud 37 of polished aluminum is provided in front of the cage assembly 33, and in close proximity to the sides of the cage, surrounding the path of parallel infrared radiation from the reflector to the sapphire window 31. This shroud reflects stray radiation when the cage assembly is in the open position allowing the reflection of radiation from the case assembly in a predetermined direction. The radiation is reflected out of the instrument cavity through the sapphire window thereby reducing the distribution of stray radiation (thus heat) within the instrument cavity. It has been found this technique reduces the heat load within the instrument cavity by at least 25 percent.

Figure 2:
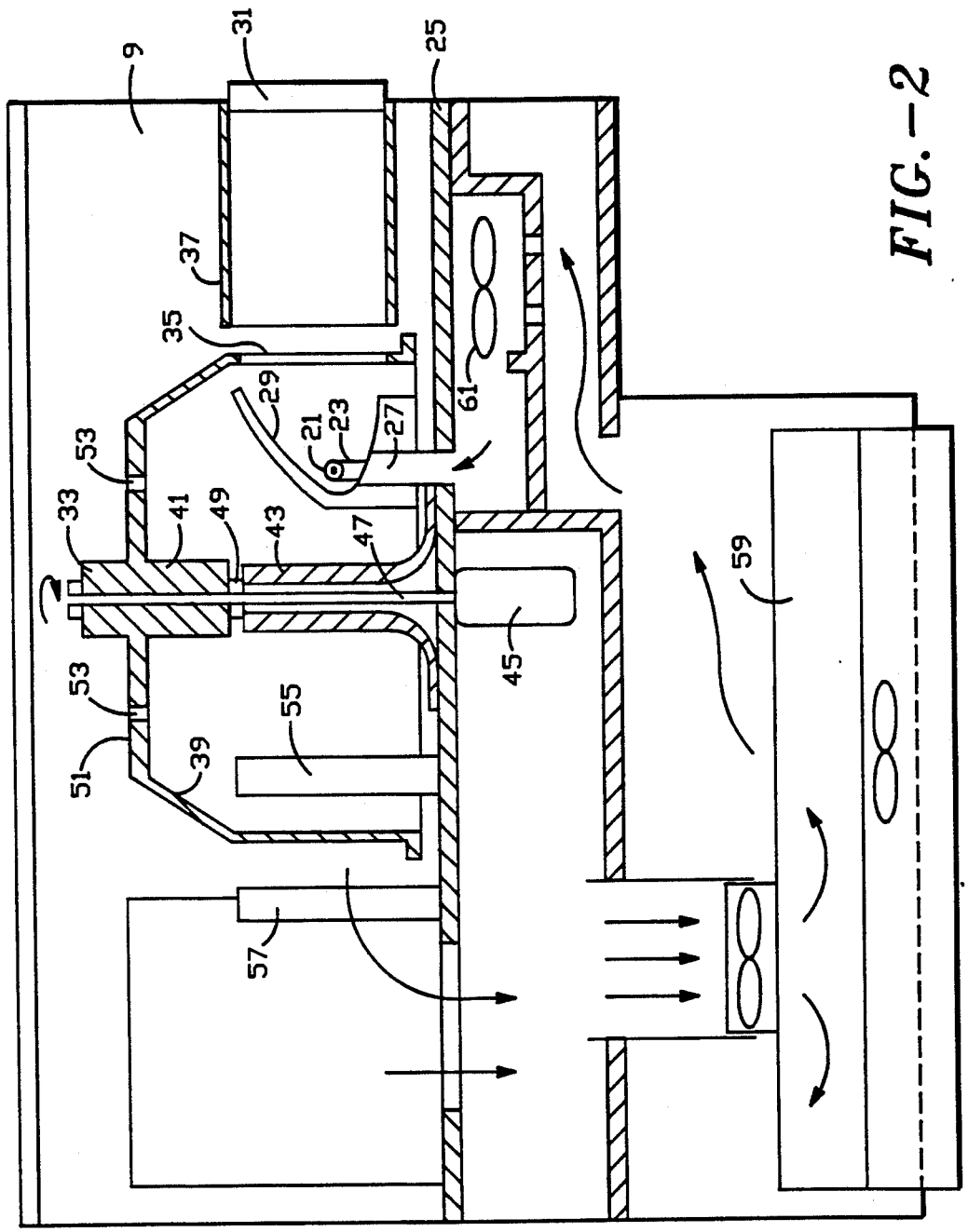
FIG. 2 is a side elevation in cross section illustrating the source instrument of the present invention at the center line thereof.
Figure 3:
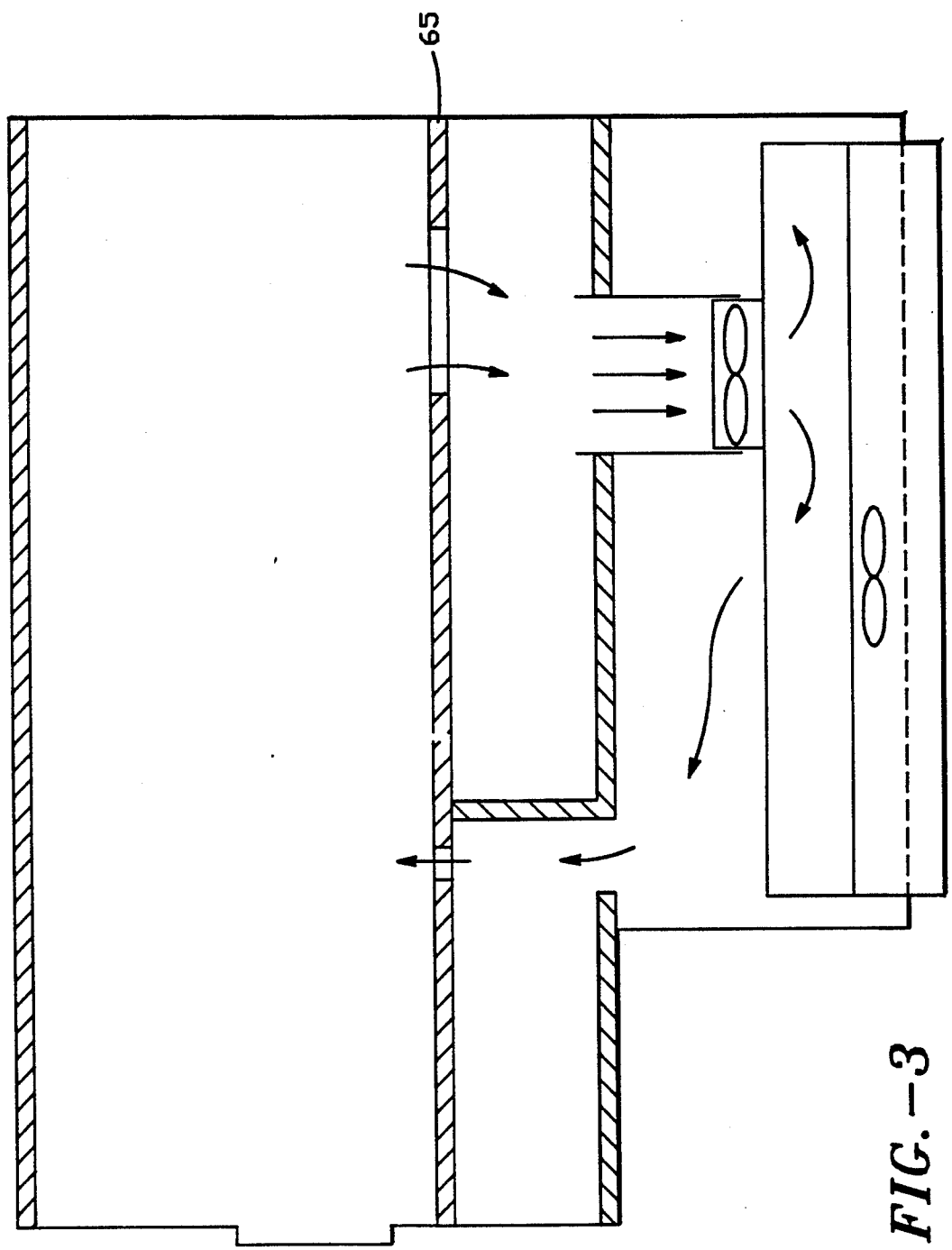
FIG. 3 is a side elevation in cross section of the cooling system of the detector instrument of the present invention at the center line thereof.

Reference is made to FIG. 2 for an understanding of the construction of the cage assembly 33. It is essentially an inverted bowl 39 mounted on a rotating center drive shaft 41. A pedestal 43 is provided which is secured to the support bench and centered over a drive motor 45 which is mounted below the bench. The drive shaft of the motor engages with an extension shaft 47 which is secured to the cage assembly which in turn is mounted on bearings 49 above the pedestal. The horizontal top surface 51 of the cage assembly is provided with threaded holes 53 for the insertion of balance screws.

The inside of the cage assembly 33 is constructed of polished aluminum such that when the cage is closed, the radiation is not totally absorbed by the cage walls but allowed to reflect between the inside of the cage and the reflector surface 29 until the cage comes open again. Although this radiation is not parallel, when the cage comes open again it is allowed to emit to the reflector shroud 37 and also exit the instrument through the sapphire window 31.

A means is provided for calculating and controlling the cage's rotational speed. In the preferred embodiment, it is an optical switch which is comprised of a light emitting diode 55 disposed inside the cage 33, on the opposite side of the support shaft 41 from the lamp 21 and reflector 29, and an optical sensor 57 disposed outside of the cage. The optical switch is actuated by the diode's light source emitting through a small hole in the cage wall as it rotates. The hole is separate from the openings 35 in the cage which allows emission of the infrared radiation. Electronic controls are provided to accurately maintain the selected speed of rotation for the motor which rotates the cage from the signals generated by the optical switch. The speed of rotation is also monitored by the computer external to the source and detector instruments of the ESR/FF and which analyzes the measurements of the ESR/FF and performs the computations the invention is designed to provide.

Also mounted on the support bench 25 inside the source instrument enclosure are power supplies for the lamp 21, the optical switch, the source instrument coolers, and the electronics.

Due to the extreme heat created by the lamp, the source instrument 15 is cooled by forced convection and appropriate ducting. Thermoelectric coolers 59 are mounted below the support bench 25 to cool nitrogen gas ($N_2$) or dry air which is routed through the source instrument by forced convection fans. One fan 61 blows nitrogen or dry air up through holes in the support bench at both ends of the lamp adjacent to the graphite rod supports 23 and along the cooling fins 27 formed thereon. This flow of cooling gas exits the cage assembly through the two open sides 35 and thereafter is returned to the thermoelectric coolers through outlet vents disposed proximate the other end of the instrument enclosure from the inlet end which is adjacent to the lamp. Additional fans are provided to maintain the flow of the cooling gas in the system. Nitrogen gas is preferred because it has essentially no absorption in the infrared region.

An electronic circuit board 63 is also mounted on the bottom side of the support bench 25 so that it remains in a cooler atmosphere like the drive motor 45 for the cage assembly. This is also true of the circulating fans and their drive motors which force the flow of cooling nitrogen gas through the ducting.

THE DETECTOR INSTRUMENT

The detector instrument 17, illustrated in FIGS. 3–6 disposed on the opposite side of the combustion gas duct 19 from the source instrument 15, consists of an optical bench 65 which supports both the optical array and other hardware. The optical array of mirrors causes the incident parallel infrared radiation from the source instrument to form a line image of finite length on a first focus point 67 and then to form a focusing image at a second focus point. This is done by an array of mirrors which fold the parallel radiation as well as focus it so that it can fit in a compact enclosure.

The infrared radiation is incident to the detector instrument 17 through a sapphire window 71 disposed in the wall of the exhaust gas duct 19 and is directed by the optical array to a rotating circular variable filter 73, hereafter referred to as the CVF, which is commercially available. The CVF is a circular optical filter, having a disk shape, made to pass radiation at unique wavelengths as a linear function of its radial position. Instead of a CVF, a diffraction grating could also be employed or a device to differentiate incidence radiation intensities by wavelength. The CVF is disposed at the first focus point 67 of the optical array, and an optical slit 75 is disposed in the path of the radiation immediately in front of the CVF. An infrared radiation detector 77 is disposed at the second focus point for receiving the filtered radiation which has passed through the CVF.

The detector optics consist of a two-axis design. One axis, called the horizontal view shown in FIG. 6, causes the radiation to form a line image of finite length on the CVF 73. The view in FIG. 6 is looking through the rear or back side of reflectors 81, 83 which are illustrated in cross sections. After the radiation passes through the CVF in the horizontal view, it is folded and converged by a series of reflectors to form a focusing image on the infrared detector 77. The other axis of the optical array illustrated in FIGS. 4 and 5, called the vertical view, causes the infrared radiation to form parallel rays in the vertical plane through the CVF and it is folded and converged by a series of reflectors to form a focusing or spot image on the infrared detector as in the horizontal view.

Figure 4:
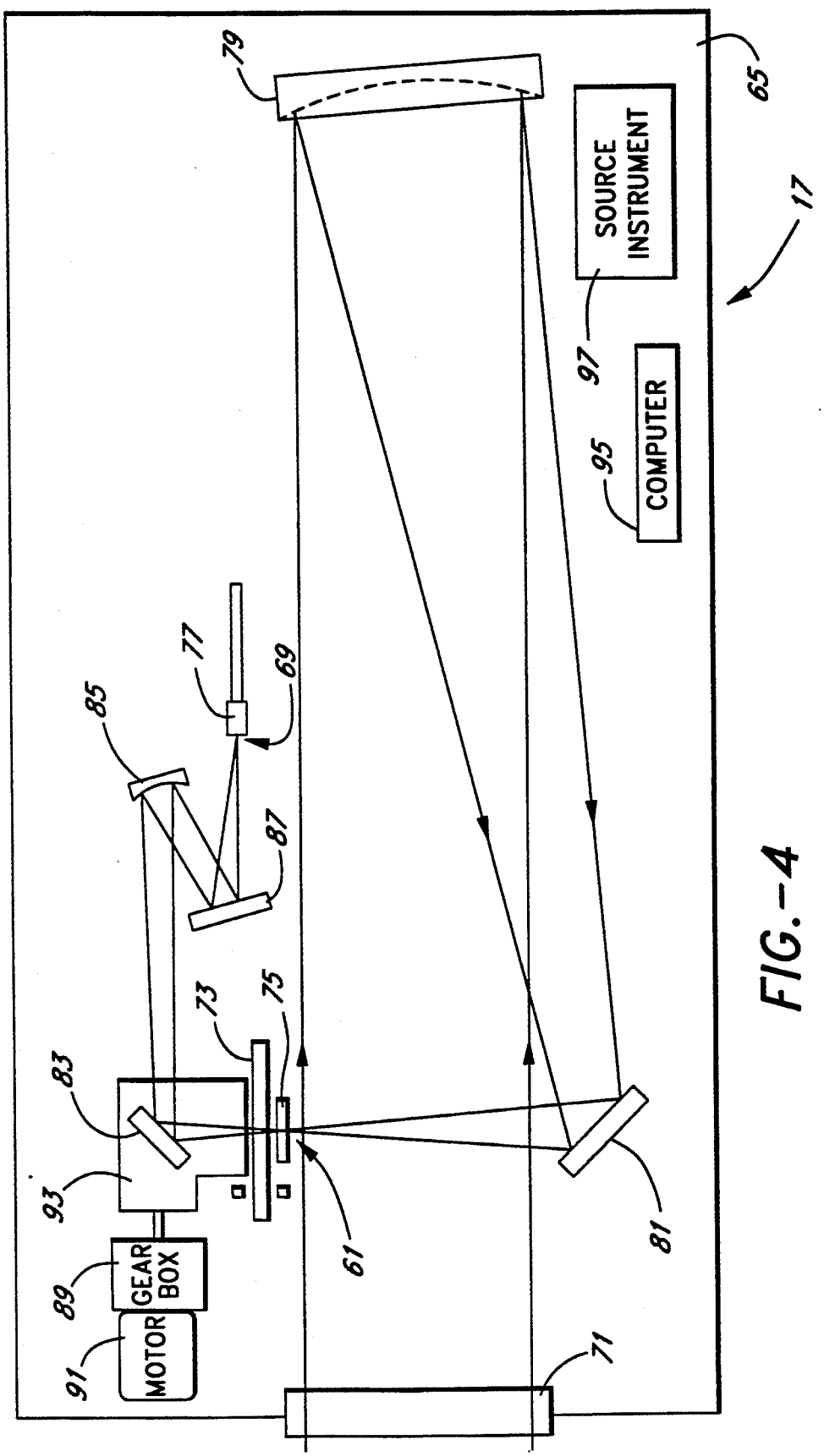
FIG. 4 is a top plan view illustrating the optical array of the detector instrument of the present invention.
Figure 5:
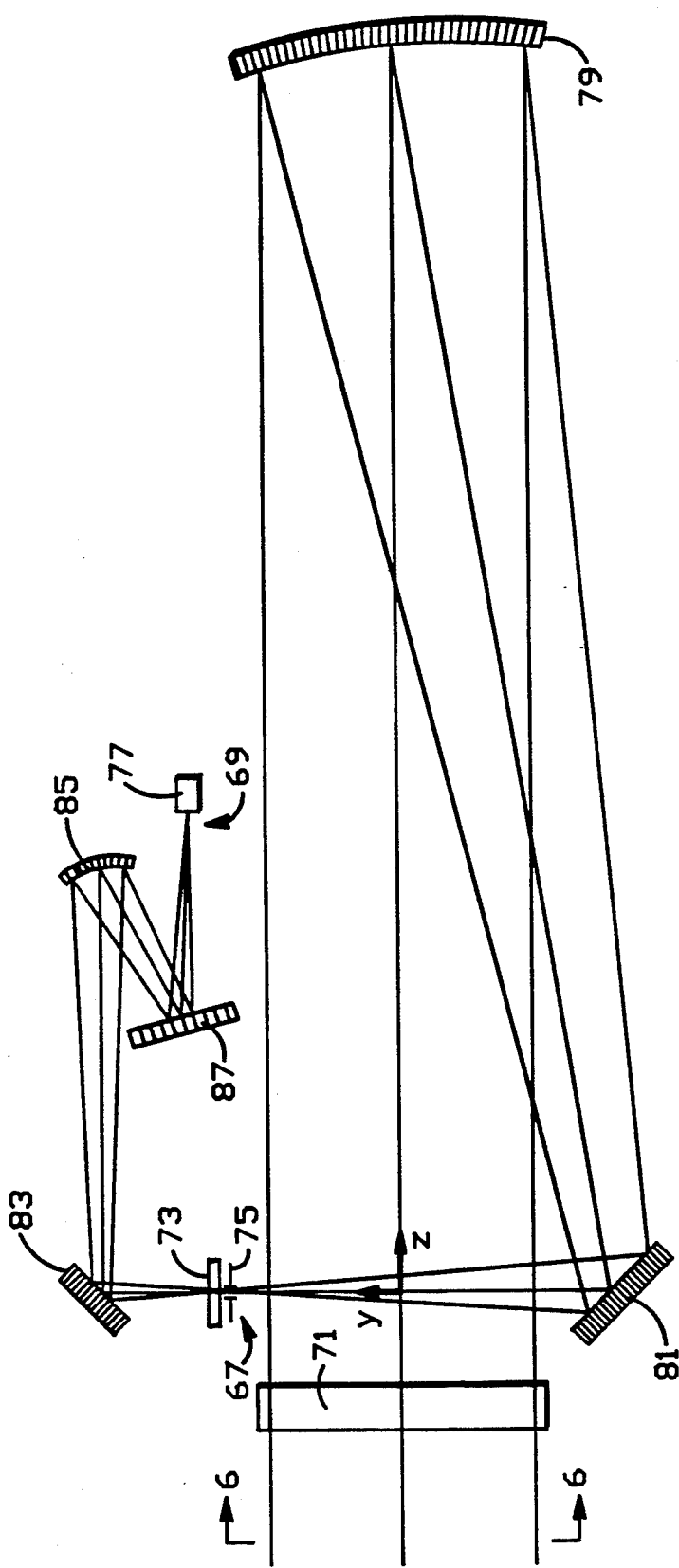
FIG. 5 is a schematic top plan view of FIG. 4.
Figure 6:
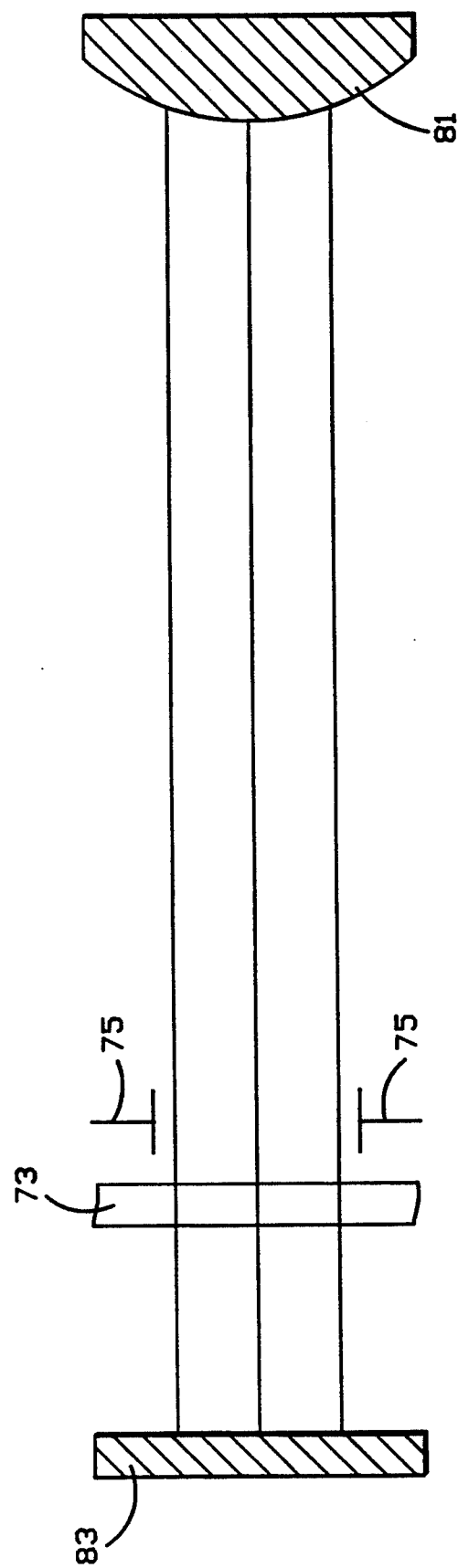
FIG. 6 is a schematic view taken along line 6—6 of FIG. 5 showing the infrared radiation in the vertical plane.

Reference is made to the top plan views, called the vertical view, FIGS. 4 and 5. The parallel infrared radiation incident through the sapphire window 71 strikes a spherical concave reflector 79 disposed on the far end of the detector optical bench 65. It is positioned to reflect in both the horizontal and vertical views to a cylindrical plano-convex reflector 81. The infrared radiation in the horizontal view is reflected parallel from this convex cylindrical surface of reflector 81 as illustrated in FIG. 6 to enter the optical slit 75 which is used to eliminate stray radiation. Then it passes through the CVF 73. The radiation is converged by the concave reflector 79 to focus on the CVF and folded by the planar surface of reflector 81 in the vertical view.

From the CVF, the radiation is redirected or turned via a first folding or flat mirror 83, then focused to the infrared radiation detector 77 by converging both the horizontal and vertical views through the use of two cylindrical plano-convex reflectors 85, 87 optically opposed to each other (rotated by 90° relative to each other). Thus, in the horizontal view, reflector 87 acts as a simple folding mirror, while reflector 85 acts to focus the horizontal view onto the detector. In the vertical view, the radiation leaving the CVF which is parallel from the cylindrical plano-convex 81 in the vertical plane, is focused to the detector using the two cylindrical plano-concave reflectors 85, 87 in like manner as for the horizontal view but in opposite relation: reflector 87 is the focusing mirror while reflector 85 is the folding mirror. All reflectors are gold platted to enhance the reflectivity of the infrared radiation.

The CVF 73 is manufactured by Optical Coating Laboratory, Inc. of Santa Rosa, Ca., and is designed to pass infrared radiation only at unique bands of wavelengths. In the present invention, it is designed to be operated between 1300 and 5500 nanometers. The CVF is rotated at 2.9 RPM by a gear box 89 and drive motor 91. The speed of rotation is designed such that the detector's natural response frequency of 750 Hz can be electronically recorded to detect radiation at the smallest practical incremental wavelength. The natural response frequency of the detector thus determines the rotational speed of the source instrument's cage assembly 33, assuming that for the present embodiment that three readings per wavelength is desired.

The infrared detector 77 is of the lead selenide type which is sensitive to radiation between 1000 to 6000 nanometers. The detector is a resistive element whose conductance increases when infrared radiation is incident on the active area. The change in conductance is manifested as a voltage change across the detector when passing a constant current through it. Thus, the measured voltage is indicative of incident radiation. The detector used in the ESR/FF instrument is manufactured by Infrared Associates, Inc. of Cranbury, N.J. The natural response of the detector produces a peak response at approximately 4300 nanometers. Through calibration procedures using the source instrument's known black body radiation spectrum, through a continuum of very low nitrogen pressure over a prototypic distance, the detector's response at any given wavelength can be normalized to that of a black body spectrum. This normalization procedure results in a correction factor, called CF($\lambda$), defined as CF($\lambda$)=I($\lambda$, normalized)/I($\lambda$, measured) where I is either the normalized black body or measured unabsorbed radiation. CF($\lambda$) can then be applied to any measured radiation signal, regardless of the temperature of the black body radiation source. Thus, any measured radiation spectrum after normalized via CF($\lambda$) can be compared to a black body radiation distribution provided its temperature is known, which substantially increases the accuracy of the instrument.

THE ELECTRONICS HARDWARE

Figure 8:
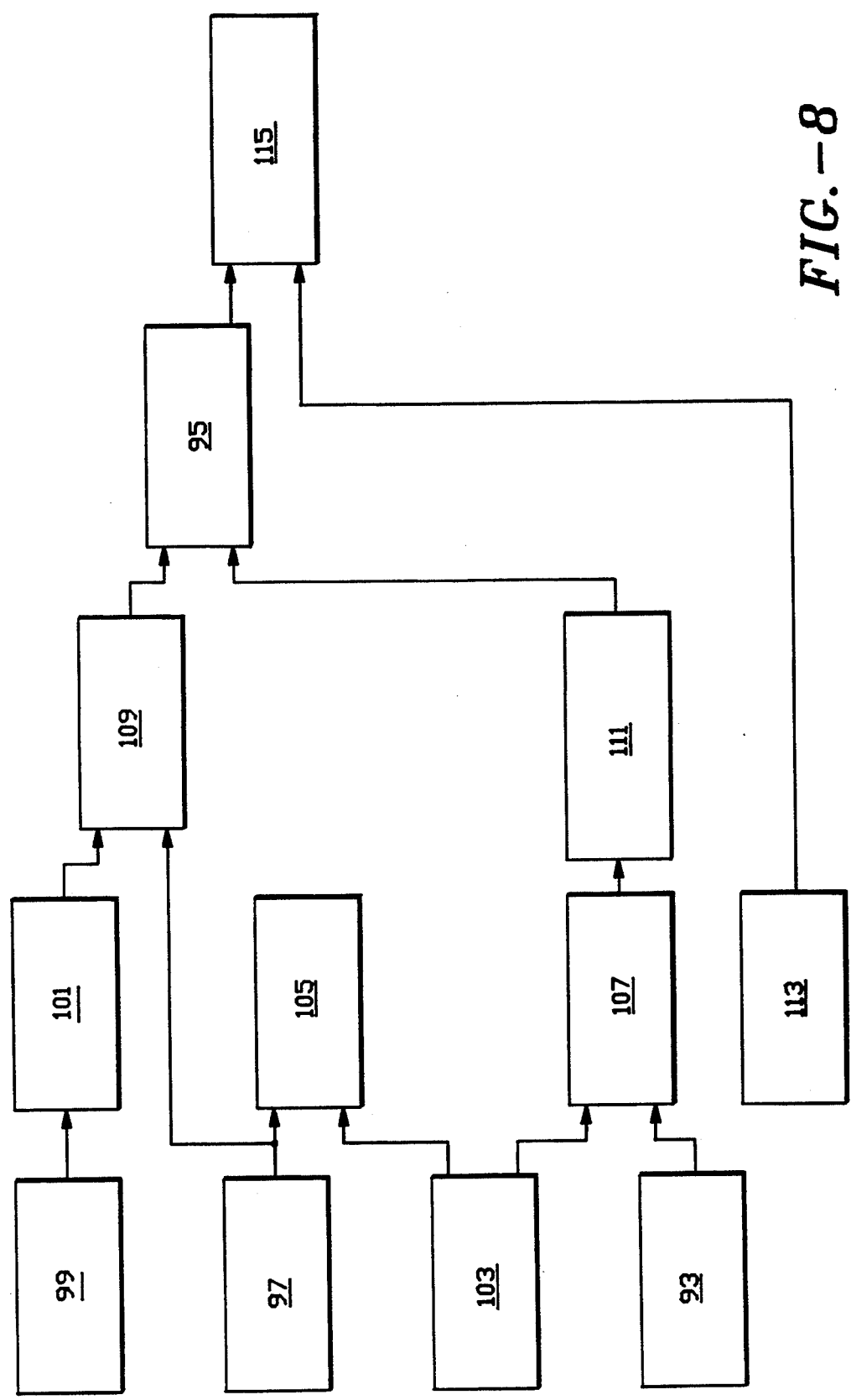
FIG. 8 is a block diagram of the electronic operation of the apparatus.

The electronic processing of the detector instrument's signals is accomplished by filtering and amplifying the analog infrared detector signal and then transmitting it and certain digital signals to a computer. The software logic used to process the signals is illustrated in FIG. 8 of the drawings.

A signal from the optical switch on the CVF 73 within the detector instrument 17, box 93, is routed to a computer, box 95, from a digital processing auxiliary computer board. This board is read by a computer program by either standard interrupt command, or by continuously monitoring a computer memory location, or directly by reading an input/output port associated with the auxiliary board. The signal from the cage optical switch 55, 57 of the source instrument, box 97, is also read in a similar manner. When the signal from the detector instrument 77 is received, a mechanism is set in motion which reads the analog signal, box 99, produced by the infrared detector, and then converts it to digital, box 101.

An internal clock function, box 103, is utilized to calculate, box 105, the rotation rate of the source instrument cage assembly 33 and to calculate, box 107, the rate of rotation of the CVF 73. The detector signal is sampled three times, box 109, which is controlled by the optical switch, box 97, in the source instrument, while the location of the CVF wavelength (position) is determined, box 111. The output signals from boxes 109 and 111 are fed into the computer, box 95, to calculate the net radiation from the source instrument.

The detector's signal is mathematically compared to standard curves which relate the source infrared radiation intensity to that produced by a black body source (i.e., the surface temperature of the source lamp 21). To do this it is necessary to calculate a black body reference spectrum, box 113. Such a comparison can be accomplished by either monitoring the voltage applied to the lamp and then correlating that voltage to the lamp's temperature or by fitting the measured radiation, at several wavelengths, which do not absorb in the continuum, to a normalized curve of infrared radiation versus wavelength. Such a curve can be constructed by integration of Planck's equation. Thus, the data analysis procedure is capable of discerning the equivalent temperature of the lamp. This is important because the accuracy of the ESR/FF instrument is dependent upon knowing accurately the magnitude of the unattended radiation from the source, called "$I_0$". Once the black body reference spectrum has been calculated, the computer can calculate the concentration of $CO_2$ and $H_2O$, box 115, from the detector signal.

Figure 9:
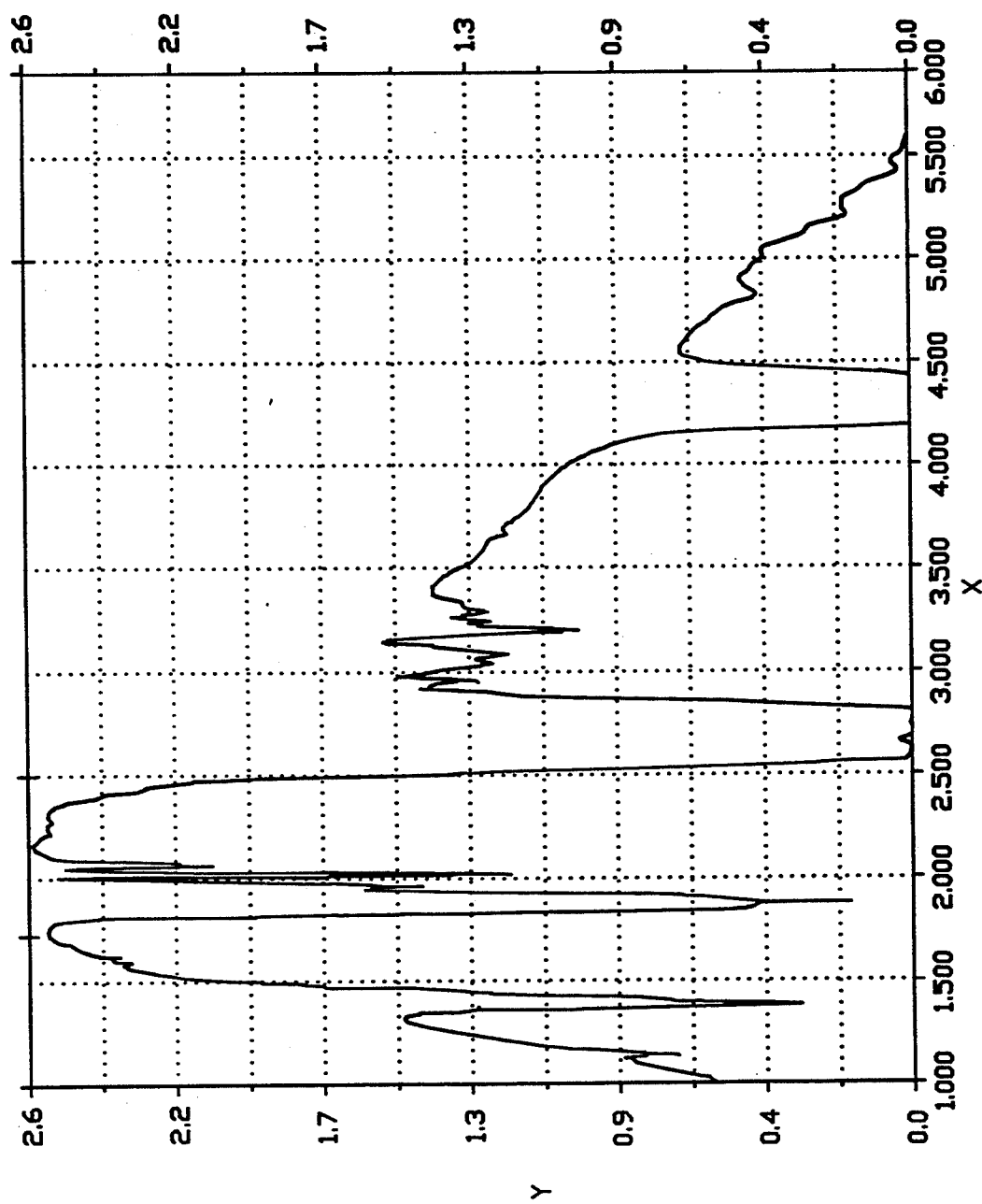
FIG. 9 is graph illustrating a typical spectral response produced by the instrument wherein both $CO_2$ and superheated water are absorbed as produced by normalizing the detected radiation to a black body curve at those wavelengths which do not absorb.

The principal of operation of the present invention depends upon the fact that while the infrared radiation passes through the gas duct, a portion of the radiation is absorbed uniquely by the species of gas in the duct. The ESR/FF instrument is designed to produce the maximum intensity radiation between 1300 nanometers and 5500 nanometers wavelength. The gas species absorbing infrared radiation in this region of the spectrum, and those appearing in large concentrations within a fossil fuel-fired boiler exhaust stack, are $CO_2$ and superheated water. (See a typical absorption spectrum for $CO_2$ and $H_2O$, FIG. 9 of the drawings. The X scale is wavelength [micrometer] and the Y scale is the radiance [watts/$CM^2$-ster-micr]) Free nitrogen gas does not absorb infrared radiation within this spectrum to any sufficient degree and therefore does not affect readings by the detector 77 which is also the reason it is used as the circulating coolant for the source instrument. Dry air can also be used for cooling since free oxygen has no absorption in the IR region and $CO_2$ concentrations are less than 0.04 percent. CO is measured by the present invention less accurately than $CO_2$ and $H_2O$, but it is of negligible concern because it is only present as a few hundred parts per million in the combustion effluent.

Figure 7:
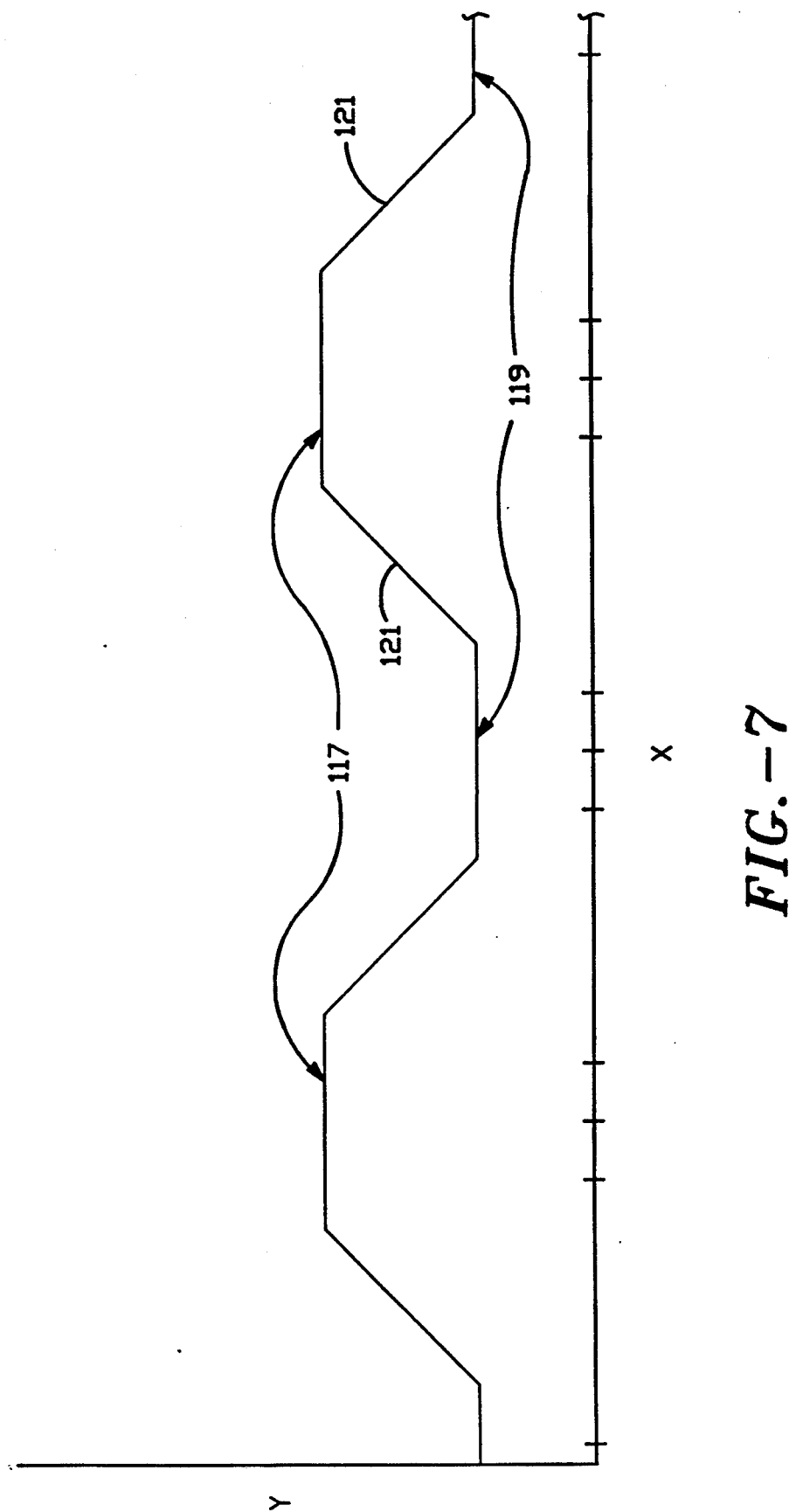
FIG. 7 is a graph showing the frequency of detector recording.

Reading the infrared detector signal on the apparatus of the present invention is unique due to the cage assembly 33 rotating about the infrared radiation source. The rotation inherently causes a non-linear response at the detector. This is because an edge on the cage's opening or closing positions passes across the source lamp 21 causing either a partial opened or partial closed position. (See the graph of FIG. 7 of the drawings which indicates this condition. The X scale is frequency of detector recording, and the Y scale is the cage door elevation with the upper flats 117 representing the open cage condition, the lower flats 119 the closed condition, and the slanted lines 121 the transition periods.) It is the object of the present invention to measure incident radiation at the detector multiple times for each full opened and for each full closed position of the cage assembly. When the cage assembly is in the open position, both infrared radiation from the source (less that radiation absorbed by the species in the continuum) and background radiation are measured. When the cage is in the closed position, only background radiation is read. The difference between these two readings is called I ($\lambda$, measured).

The concentration of the species of gas, the variable N, in the continuum is computed in the standard fashion using Beer's Law:

$$I = I_0 e^{-\alpha N x}$$

where $\alpha$ = absorption coefficient unique to each species and wavelength, N = molecular density of a given species, and x = distance between the source and the detector. "I" refers to I (normalized) and "$I_0$" refers to the calculated spectrum via Planck's equation at a given black body temperature.

The ambient temperature within the source and detector instrument cavities, the operating temperature of the detector, cage rotational speed, CVF rotational speed, along with vibration data associated with the cage assembly rotation, combustion exhaust gas temperature data, and other readings are taken and imput into the electronic processing for measurement of deviation against standards.

Operation of the apparatus of the present invention provides a continuous, very accurate analysis of the concentrations of $CO_2$ and superheated water in the combustion effluents for permitting accurate thermodynamic analysis of the mass fuel flow and the thermodynamic efficiency of the steam generation system.

Thus it will be apparent from the foregoing description of the preferred embodiment that all of the objects and advantages of the invention are achieved. While the preferred embodiment of the invention has been described in considerable detail herein, the invention is not to be limited to such details as have been set forth except as may be necessitated by the appended claims.

We claim:

1. An emissions spectral radiometer including a source instrument located on one side of an exhaust gas duct and a detector instrument located on an opposite side of said duct from said first side, said instruments comprising:

in said source instrument:
 a radiation source producing pure black body infrared radiation,
 a reflector which produces parallel radiation from said source and directs it across the exhaust gas duct,
 a rotating cage assembly which encloses the radiation source and said reflector, said cage assembly having at least one opening therein aligned with said reflector to allow the parallel radiation to escape from the cage assembly as it rotates to provide an alternating flow of radiation across the exhaust gas duct, and in said detector instrument:
 an array of optical reflectors which causes the parallel radiation to form a line image of finite length at a first focus point and then to form a spot image at the second focus point,
 a rotating circular variable filter disposed at said first focus point for processing said radiation,
 an optical slit located immediately in front of said circular variable filter to intercept stray radiation, and
 an infrared radiation detector disposed at the second focus point for receiving radiation which has passed through said circular variable filter and producing an electronic signal output for input to a computer.

2. The spectral radiometer of claim 1 wherein the optical array of said detector instrument includes a folding mirror which folds the infrared radiation emission received from said source instrument to permit said detector instrument to be contained in a compact enclosure.

3. The spectral radiometer of claim 1 wherein the cage assembly includes an optical switch comprised of a light emitting diode located inside the cage assembly and an optical sensor located outside the cage assembly which is actuated by rotation of the cage assembly allowing the light emitting diode to activate and deactivate the switch resulting in an on-off flow of current through the switch thereby controlling the cage assembly speed of rotation.

4. The spectral radiometer of claim 1 wherein the source instrument is cooled by a circulating flow of gas which is refrigerated by thermoelectric coolers.

5. The spectral radiometer of claim 1 including a reflector shroud for directing the infrared radiation from the cage assembly to a sapphire window in the exhaust gas duct.

6. The spectral radiometer of claim 1 including a support bench which supports the radiation source, the reflector, the cage assembly, a light emitting diode inside the case assembly, and optical sensor which is actuated by the rotation of the cage assembly allowing said diode to alternately activate and deactivate said sensor, and a reflector shroud for directing the infrared radiation, means are provided below the support bench for rotating the cage assembly, controlling the source instrument operation, and cooling the source instrument with a flow of gas which circulates above and below the support bench.

7. The spectral radiometer of claim 1 wherein the optical array in the detector instrument includes:
 a spherical concave mirror which is positioned to reflect in both horizontal and vertical view to a cylindrical plano-convex reflector, the infrared radiation in the vertical view being reflected parallel from the cylindrical plano-convex reflector to enter the optical slit, and
 a pair of cylindrical plano-concave reflectors optically opposed to each other which focus the infrared radiation on the detector by folding and converging the radiation.

8. The spectral radiometer of claim 1 wherein the infrared source is heated to between 1100 to 1700 degrees Kelvin and has an emissivity of at least 0.90, the cage assembly has two openings and is rotated at 2250 RPM, the circular variable filter operates between 1300 and 5500 nanometers and is rotated at a speed to have a natural response frequency, and the infrared detector is sensitive to radiation between 1000 and 6000 nanometers.

9. An emissions spectral radiometer including a source instrument disposed on one side of an exhaust gas duct and a detector instrument disposed on an opposite side of said duct from said first side, said instruments comprising, in said source instrument:
 a radiation source heated to between 1000 and 1700 degrees Kelvin and producing pure black body infrared radiation having an emissivity of at least 0.90,
 a reflector which produces parallel radiation from said source and directs it across the combustion exhaust gas duct,
 a rotating cage assembly which encloses said radiation source and said reflector, said cage assembly having at least one opening therein aligned with said reflector to allow the parallel radiation to escape from the cage assembly as it rotates to provide an alternating flow of radiation across the exhaust gas duct,
 an optical switch including a light emitting diode located inside the cage assembly and an optical sensor located outside of the cage assembly which is actuated by rotation of the cage assembly allowing the light emitting diode to activate and deactivate the optical sensor resulting in an on-off flow of current through the switch thereby controlling the cage assembly speed of rotation.
 a reflector shroud for directing the infrared radiation from the cage assembly to a sapphire window disposed in the exhaust gas duct, and cooling means for the source instrument utilizing a circulating flow of gas which is refrigerated by thermoelectric coolers, and in said detector instrument;

an array of optical reflectors which causes the parallel radiation to form a line image of finite length at a first focus point and then to form a focusing image at a second focus point, said optical array including:

a spherical concave mirror which is positioned to reflect in both horizontal and vertical views to a cylindrical plano-convex reflector, the infrared radiation in the vertical view being reflected parallel from the cylindrical plano-convex reflector to focus at the first focus point, and a pair of cylindrical plano-concave reflectors optically opposed to each other which focus the infrared radiation on the detector by folding and converging the radiation, a rotating circular variable filter disposed at said first focus point for allowing only specific radiation to pass therethrough and which operates between 1300 and 5500 nanometers and is rotated at a speed to have a natural response frequency, an optical slit located immediately in front of said circular variable filter to intercept stray radiation reflected by said cylindrical plano-convex reflector, and an infrared radiation detector disposed at the second focus point for receiving radiation which has passed through said circular variable filter and producing an electronic signal output for input to a computer, said detector being sensitive to radiation between 1000 and 6000 nanometers.

* * * * *